United States Patent [19]

Lin et al.

[11] Patent Number: 5,105,015
[45] Date of Patent: Apr. 14, 1992

[54] SYNTHESIS OF NON-CYCLIC ALIPHATIC POLYAMINES

[75] Inventors: You-Jyh Lin, Columbia; Stephen R. Schmidt, Silver Spring; Ramin Abhari, Columbia, all of Md.

[73] Assignee: W. R. Grace & Co.-Conn., New York, N.Y.

[21] Appl. No.: 709,944

[22] Filed: Jun. 4, 1991

[51] Int. Cl.$^5$ .......................................... C07C 209/48
[52] U.S. Cl. ........................................ 564/492; 564/491
[58] Field of Search ................................. 564/491, 492

[56] References Cited

U.S. PATENT DOCUMENTS

| | | | |
|---|---|---|---|
| 2,502,348 | 3/1950 | Scraibine et al. | 502/315 |
| 3,232,888 | 2/1966 | Adam | 564/492 |
| 3,565,957 | 2/1971 | Mirviss | 564/491 |
| 3,733,325 | 5/1973 | Yeakey | 544/402 |
| 4,140,720 | 2/1979 | Drake | 564/491 |
| 4,235,821 | 11/1980 | Butte, Jr. et al. | 564/491 |
| 4,248,799 | 2/1981 | Drake | 564/491 |
| 4,254,059 | 3/1981 | Grey et al. | 564/492 |
| 4,375,003 | 2/1983 | Allain et al. | 564/491 |
| 4,480,051 | 10/1984 | Wu | 502/338 |
| 4,491,673 | 1/1985 | Cutchens et al. | 564/492 |
| 4,721,811 | 1/1988 | Sherwin et al. | 564/491 |
| 4,885,391 | 12/1989 | Herkes | 564/491 |

FOREIGN PATENT DOCUMENTS 2285921 12/1987 Japan .................................. 564/491

*Primary Examiner*—Richard L. Raymond
*Assistant Examiner*—Scott C. Rand
*Attorney, Agent, or Firm*—Beverly K. Johnson

[57] ABSTRACT

An improved process for selectively forming noncyclic, aliphatic polyamines from the corresponding aliphatic polynitriles by reacting the polynitrile with hydrogen at low temperature under a pressure of from 50 to 5,000 psi in a fixed bed reactor while continuously contacting the reactants with granular chromium and nickel promoted Raney ® cobalt packed therein.

17 Claims, No Drawings

SYNTHESIS OF NON-CYCLIC ALIPHATIC POLYAMINES

BACKGROUND OF THE INVENTION

This invention relates to an improved process of forming noncyclic, aliphatic compounds having a multiplicity of primary amino groups in high yields and selectivity from corresponding polynitriles.

The hydrogenation of nitriles to amines using conventional hydrogenation catalysts is well known. However, it is recognized that this synthetic mode is not an effective process for forming noncyclic, aliphatic compounds from polynitriles having an atomic structure capable of forming cyclic or ring containing compounds.

The classic method for converting nitriles to amines has heretofore involved using hydrogenation catalysts in the form of finely-divided particles in a batch or slurry process. The batch reactor is by conventional design a fixed pressurized vessel in which all of the reactants are initially charged into the reaction vessel and all of the primary amine product is retained within the vessel until the process is terminated. As the nitrile is converted to imine intermediate, the imine tend to react with previously formed amine contained within the vessel as a by-product formation and thereby detract from the overall selectivity for the desired materials. Thus, when polynitriles are converted into polyamines using a conventional batch process, one conventionally obtains large amounts of cyclic product as well as methylated secondary amines and condensation by-products.

A further disadvantage of the batch process is the substantial capital equipment cost attributed to the large reactor size which is required to afford economic feasibility on an industrial scale and which is also necessary to accommodate the agitation equipment required in slurry reactors. Removal of the slurry catalyst also increases the downstream recovery costs in conventional batch processes.

Accordingly, it is desirable to find economically feasible and safe processes for forming, in high selectivity and yields, noncyclic aliphatic polyamines from the corresponding polynitriles. The desired linear polyamines have known usefulness as chelating and sequestering agents and as reagents in the formation and cross-linking of polymeric products, such as polyurethane and polyamines.

An object of this invention is to provide a process for the production of noncyclic, aliphatic amines in high yields and selectivity from the corresponding polynitriles.

It is also an object of the invention to provide an improved process for the hydrogenation of nitriles to noncyclic, aliphatic amines using nickel and chromium promoted Raney ® cobalt catalyst under low pressure in a fixed bed, which process is more economical and efficient than conventional batch processes.

Other important objects of this invention will become apparent from the ensuing description and appended claims.

SUMMARY OF THE INVENTION

The present invention is directed to a means for providing noncyclic, aliphatic polyamines in high yields and selectivity. The object of the invention is accomplished by the hydrogenation of a noncyclic polynitrile using a promoted Raney ® cobalt catalyst in a fixed bed reactor to produce compounds having a plurality of amino groups corresponding to the polynitrile structure, wherein each nitrile is converted into a primary $-CH_2NH_2$ group.

The term "polynitrile" as used herein and in the appended claims defines compounds having at least two cyano groups separated by an immediate chain of two or more atoms. The cyano groups may be separated by hydrocarbon chains which are saturated or contain olefinic (ethylenic) unsaturation therein or may contain a heteroatom such as nitrogen, oxygen, sulfur, and the like or combinations thereof. The present invention is particularly suitable to convert adiponitrile to hexamethylenediamine. Other suitable polynitriles include nitrilotriacetonitrile, iminodiacetonitrile, ethylenediaminetetraacetonitrile, oxidiaoetonitrile, thiodiaoetonitrile, 2-methylglutaronitrile and 1,3-dicyanopropene. These compounds are normally viewed as having the proper atom chain length to intramolecularly react and form stable cyclic compounds as the dominant product. However, the present process provides a means to selectively cause the dominant product to be an aliphatic, noncyclic polyamine.

The term "polyamine" as used herein and in the appended claims refers to compounds having a plurality of amino groups corresponding to the polynitrile structure, above, wherein each nitrile is converted into a primary $-CH_2NH_2$ group.

DETAILED DESCRIPTION OF THE INVENTION

The present process involves contacting a polynitrile with granular chromium and nickel promoted Raney ® cobalt under a hydrogen pressure of from 50 to 5,000 psi in the presence of ammonia which is introduced as part of the feed material. The process must be carried out in a fixed bed reactor having the promoted Raney ® cobalt as its packing and passing the reactants through the reaction zone, preferably in a bubble bed mode.

The catalyst of the present invention is a granular chromium and nickel promoted Raney ® cobalt, which is formed from an initial alloy which contains from 45 to 62 weight percent aluminum, from 34 to 53 weight percent cobalt, from about 1 to 2 weight percent nickel and from about 1 to 2 weight percent chromium. The most preferred catalyst is formed from alloys having from about 1.0 to 1.5 weight percent each of nickel and chromium.

The catalyst is prepared by contacting the starting alloy with an aqueous solution containing from 5 to 30 weight percent of an alkali or alkaline earth metal hydroxide, preferably sodium hydroxide. The alloy should be granular, that is, have a particle size from about 0.025 to 0.5 inch, preferably from about 0.09 to 0.35 inch, mean diameter. The activation is carried out in known manners by contacting the starting alloy with normally from 1 to 20 weight percent, preferable from 3.5 to 15 weight percent, of a dilute alkaline solution while maintaining a temperature below 70° C., preferably below 50° C. Generally, it is preferred to activate the alloy at a temperature of about 35° to 45° C. Activation is readily monitored by the evolution of hydrogen and the soluble aluminum content of the alkaline solution. The process provides a suitable catalyst when 20 to 50 percent, preferably when 30 to 42 percent, of the original aluminum is removed. The activated promoted Raney ® cobalt catalyst is washed with water to free it from the alkaline solution and used immediately or stored under water in an inert atmosphere until needed.

The hydrogenation process of the invention is carried out by using a fixed bed reactor packed with the above-described granular chromium and nickel promoted Raney ® cobalt catalyst through which the polynitrile reactant and ammonia are passed. Suitable fixed bed reactors include, but are not limited to, bubble bed and trickle reactors.

The polynitrile must be introduced into the reactor as a liquid feed. That is, when the polynitrile is in liquid form, the polynitrile may be used alone or with a small amount, e.g., 0–10 percent by weight, of a miscible co-solvent such as water. When the polynitrile is in solid form, the polynitrile is introduced as a solution dissolved in a solvent medium. Solvents suitable for this purpose include alcohols such as methanol, ethanol, isopropanol, n-butanol and the like; amides such as N,N-dimethylacetamide, formamide, N,N-dimethylformamide and the like; ethers such as dioxane and the like as well as other solvents which are inert to the reactants and the products in the reaction zone and are capable of remaining liquid under the reaction conditions. It is preferred that the polynitrile be introduced as a solution at concentrations of from 5 weight percent to saturation, preferably from 5 to 30 weight percent based on the total weight of the liquid solution introduced into the reaction zone.

The polynitrile is introduced into the packed reactor as a liquid feed at a flow rate of from about 0.02 to 10, preferably from about 0.05 to 2, grams of polynitrile/min-cm$^2$. Ammonia, polynitrile and, where applicable, solvent should be maintained in a liquid state in the reaction zone. The liquids should be introduced and flow cocurrently through the reactor. Preferably, hydrogen gas is introduced and caused to pass through the reaction zone cocurrently with the liquids. The granular and high surface area characteristics required of the catalyst, when combined with the relatively low flow rate discussed above, provide the required very high ratio of catalyst surface area to polynitrile reactant.

The polynitrile is contacted with the granular chromium and nickel promoted Raney ® cobalt catalyst in the presence of hydrogen and ammonia as described above. The hydrogen gas is introduced into the reaction zone at a rate sufficient to maintain a hydrogen pressure in the reaction zone of from 50 to 5,000 psi, preferably from 300 to 3,000 psi. The pressure maintained in the reaction zone should be sufficient to maintain all of the reactants, the polynitrile, the ammonia and, when applicable, the solvent in a liquid state as described above. The hydrogen pressure described above may be supplemented by partial pressure formed from an inert gas such as nitrogen.

The reaction zone should be maintained at an elevated temperature of from 30° to about 200° C. with from 60° to 125° C. being preferred. The ammonia utilized in the present process may be introduced into the reactor as part of the liquid feed or permitted to flow cocurrently with the polynitrile at a flow rate of from 0.5 to 20, preferably 2–10, g/min-cm$^2$. The ammonia should be present in the reaction zone in at least 5% by weight based on the weight of the polynitrile and may be present in excess of the polynitrile including being the solvent media for the polynitrile.

The liquids are preferably introduced into the reaction zone along with the hydrogen gas in a manner to cause them to flow cocurrently. The hydrogen is introduced in a volume flow rate of from 100 to about 3,000, preferably from 300 to 2,000 standard cubic centimeter per minute-centimeter squared (scc/min-cm$^2$) and a total liquid volumetric flow ranging from 0.1 to about 50, preferably from 0.2 to about 20 cc/min-cm$^2$. These rates have presently been found to provide sufficient flow of the polynitrile over the modified Raney ® cobalt catalyst to aid in providing a high catalyst to nitrile ratio. The residence time should be sufficient to produce an aliphatic polyamine as the dominant reaction product. For example, a residence time of from about 2 to 40 minutes, preferably from 5 to 20 minutes, is normally sufficient for a bubble bed type reactor.

The process of the invention can be used for hydrogenation of various polynitriles to noncyclic, aliphatic amines. It is understood that the specific polynitrile reactant chosen will determine the primary amine product to be formed. Each cyano group will be converted to a primary methyleneamine group. It has been found that when using the present process, the hydrogenation selectivity goes to the formation of primary amine product without major interaction between the formed methyleneamine and the intermediate imine groups and especially substantially low intramolecular reaction.

The following examples are given for illustratively purposes only and are not meant to be a limitation on the present invention except as defined by the claims appended hereto. All parts and percentages are by weight unless otherwise stated.

EXAMPLE I

Hydrogenation of adiponitrile ("ADN") was carried out using a bubble bed tubular reactor fabricated from 316 stainless steel tubing of ½ inch outside diameter, 0.43 inch inside diameter and about 2 feet long. The reactor was positioned vertically with an inlet feed tube located at its bottom for each of the feed materials to be supplied through the pressure pumps and the pressure controlled by a back pressure regulator. The reactor was packed with chromium and nickel modified Raney ® cobalt catalyst and maintained at an oven temperature of 125° C.

The granular promoted Raney ® cobalt catalyst was prepared by treating a granular alloy of aluminum, cobalt, chromium and nickel (60/38/1/1) of about 5 to 8 mesh (U.S. standard size) with dilute sodium hydroxide (averaging about 4 weight percent) at a temperature of 38±2° C. Activation was continued until about 35% of the original aluminum in the alloy was removed (based on the final aluminum content of the alkaline solution). The activated granules were washed with water until the effluent pH was about 8.5 and then used immediately or stored under water in the absence of air until needed for use.

AND was introduced into the reactor at a liquid flow rate of 0.55 g/min into the tubular reactor. Ammonia was introduced into the reactor simultaneously at a feed rate of 3.1 g/min. Hydrogen was cocurrently fed into the reactor with AND and ammonia at a rate of 1000 scc/min. The reactor pressure was maintained at about 1,000 psi.

The reactor products were analyzed by gas chromatography and it was determined that there was a 100% conversion of adiponitrile with molar selectivity to the desired hexamethylenediamine being 95.8% with only 1.9% hexamethyleneimine and 2.3% bis(hexamethylene)triamine formed.

EXAMPLE II

The process of Example I above was repeated except that the oven temperature was maintained at 114° C. instead of 125° C. The products were analyzed by gas chromatography and the conversion was determined to be 100% with molar selectivity of the linear product, hexamethylenediamine being 94.7% with only 1.4% hexamethyleneimine, 1.3% bis(hexamethylene)triamine and 2.2% of aminocapronitrile.

EXAMPLE III

The process of Example I above was repeated except that the oven temperature was maintained at 60° C. instead of 125° C. The products were analyzed by gas chromatography and the conversion was determined to be 100% conversion with 100% molar selectivity for the desired hexamethylenediamine.

EXAMPLE IV

The process of Example I above was repeated except that the tubular reactor length was 1 foot and the oven temperature was maintained at 109° C. instead of 125° C. The products were analyzed by gas chromatography and the conversion was determined to be 96% with molar selectivity of the linear product, hexamethylenediamine being 71% with only 1.4% hexamethyleneimine and 23% of aminocapronitrile.

The invention which is intended to be protected herein is not to be construed as limited to the particular principles and modes of operation disclosed, since these are regarded as illustrative rather than restrictive. Variations and changes may be made by those skilled in the art without departing from the spirit of the invention.

We claim:

1. A process for converting polynitriles to noncyclic aliphatic compounds having a plurality of primary amino groups comprising
   a) introducing into a fixed bed reactor having a granular chromium and nickel promoted Raney ® cobalt packing therein, a liquid feed of an aliphatic polynitrile and at least about 5 weight percent based on the polynitrile of ammonia;
   b) contacting the polynitrile with the chromium and nickel promoted Raney ® cobalt in the presence of hydrogen pressure of from about 50 to about 5,000 psi for a time and temperature sufficient to produce noncyclic aliphatic compounds having a plurality of primary amino groups as the dominant product; and
   c) recovering said noncyclic aliphatic polyamines.

2. The process of claim 1 wherein said polynitrile in said reactor is maintained at a flow rate of from 0.02 to 10 gm of polynitrile per min-cm$^2$ and said polynitrile, ammonia, hydrogen, and chromium and nickel promoted Raney ® cobalt are maintained in said reactor under bubble bed conditions.

3. The process of claim 1 wherein the hydrogen and ammonia are passed through the reactor cocurrently with the polynitrile; that the hydrogen flow rate is from 100 to 3,000 scc/min-cm$^2$; the hydrogen pressure is at least 50 psi; and the total liquid flow rate is from 0.1 to 50 cc/min-cm$^2$.

4. The process of claim 2 wherein the hydrogen is passed through the reactor cocurrently with the polynitrile; that the hydrogen flow rate is from 100 to 3,000 scc/min-cm$^2$; the hydrogen pressure is at least 50 psi; and the total liquid flow rate is from 0.1 to 50 cc/min-cm$^2$.

5. The process of claim 1 wherein the promoted Raney ® cobalt has a particle size of from 0.025 to 0.5 inch mean diameter and is formed by removal of from 20 to 50% of the aluminum from an initial alloy composed of about 45 to 62 wt. % aluminum, about 34 to 53 wt. % cobalt, about 1 to 2 wt. % chromium and about 1 to 2 wt. % nickel.

6. The process of claim 2 wherein the promoted Raney ® cobalt has a particle size of from 0.025 to 0.5 inch mean diameter and is formed by removal of from 20 to 50% of the aluminum from an initial alloy composed of about 45 to 62 wt. % aluminum, about 34 to 53 wt. % cobalt, about 1 to 2 wt. % chromium and about 1 to 2 wt. % nickel.

7. The process of claim 3 wherein the promoted Raney ® cobalt has a particle size of from 0.025 to 0.5 inch mean diameter and is formed by removal of from 20 to 50% of the aluminum from an initial alloy composed of about 45 to 62 wt. % aluminum, about 34 to 53 wt. % cobalt, about 1 to 2 wt. % chromium and about 1 to 2 wt. % nickel.

8. The process of claim 1 wherein the reactor is maintained at a temperature of from about 60° C. to about 125° C.; the polynitrile is introduced into the reactor at a flow rate of from 0.05 to 2 gm/min-cm$^2$; and the hydrogen pressure is from about 300 to 3,000 psi.

9. The process of claim 2 wherein the reactor is maintained at a temperature of from about 60° C. to about 125° C.; the polynitrile is introduced in the reactor at a flow rate of from 0.05 to 2 gm/min-cm$^2$; and the hydrogen pressure is from about 300 to 3,000 psi.

10. The process of claim 1 wherein the polynitrile is adiponitrile and the major recovered product is hexamethylenediamine.

11. The process of claim 2 wherein the polynitrile is adiponitrile and the major recovered product is hexamethylenediamine.

12. The process of claim 6 wherein the polynitrile is adiponitrile and the major recovered product is hexamethylenediamine.

13. The process of claim 9 wherein the polynitrile is adiponitrile and the major recovered product is hexamethylenediamine.

14. The process of claim 1 wherein the granular promoted Raney ® cobalt is of a particle size of from about 0.09 to 0.35 inch mean diameter and contains up to about 2 weight percent of chromium and nickel, respectively, the ammonia is present in a molar excess to the polynitrile reactant, the hydrogen pressure is from 300 to 3,000 psi, the polynitrile reactor flow rate is from 0.05 to 2 g of polynitrile/min-cm$^2$, the reactor temperature is maintained at from about 60° C. to 125° C. and the hydrogen, ammonia and polynitrile flow cocurrently through the reactor.

15. The process of claim 2 wherein the granular promoted Raney ® cobalt is of a particle size of from about 0.09 to 0.35 inch mean diameter and contains up to about 2 weight percent of chromium and nickel, respectively, the ammonia is present in a molar excess to the polynitrile reactant, the hydrogen pressure is from 300 to 3,000 psi, the polynitrile reactor flow rate is from 0.05 to 2 g of polynitrile/min-cm$^2$, the reactor temperature is maintained at from about 60° C. to 125° C. and the hydrogen, ammonia and polynitrile flow cocurrently through the reactor.

16. The process of claim 6 wherein the granular promoted Raney ® cobalt is of a particle size of from about 0.09 to 0.35 inch mean diameter and contains up to about 2 weight percent of chromium and nickel, respectively, the ammonia is present in a molar excess to the polynitrile reactant, the hydrogen pressure is from 300 to 3,000 psi, the polynitrile reactor flow rate is from 0.05 to 2 g of polynitrile/min-cm$^2$, the reactor temperature is maintained at from about 60° C. to 125° C. and the hydrogen, ammonia and polynitrile flow cocurrently through the reactor.

17. The process of claim 9 wherein the granular promoted Raney ® cobalt is of a particle size of from about 0.09 to 0.35 inch mean diameter and contains up to about 2 weight percent of chromium and nickel, respectively, the ammonia is present in a molar excess to the polynitrile reactant, the hydrogen pressure is from 300 to 3,000 psi, the polynitrile reactor flow rate is from 0.05 to 2 g of polynitrile/min-cm$^2$, the reactor temperature is maintained at from about 60° C. to 125° C. and the hydrogen, ammonia and polynitrile flow cocurrently through the reactor.

\* \* \* \* \*